United States Patent
Steegers-Theunissen et al.

(10) Patent No.: US 6,576,634 B1
(45) Date of Patent: Jun. 10, 2003

(54) PHARMACEUTICAL OR DIETETIC PREPARATION FOR IMPROVEMENT OF FERTILITY AND SPERM QUALITY

(75) Inventors: Regine Patricia Maria Steegers-Theunissen, Nijmegen (NL); Robert Johan Joseph Hageman, Waddinxveen (NL); Arie Nieuwenhuizen, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/610,536

(22) Filed: Jul. 7, 2000

(51) Int. Cl.$^7$ ............ A61K 31/495; A61K 31/50; A61K 33/32
(52) U.S. Cl. ............ 514/249; 514/929; 424/641; 424/643
(58) Field of Search ............... 514/249, 929; 424/641, 643

(56) References Cited

U.S. PATENT DOCUMENTS 5,992,704 A * 11/1999 Bland .................... 514/185

OTHER PUBLICATIONS

Wong et al., Male factor subfertility: possible causes and the impact of nutritional factors, Fertility and Sterility, 2000 73/3 (435–447).*

Mathur et al., The Effect of Aminopterin induced folic acid deficiency on spermatogenesis, Fertility and Sterility, 1977 28/12 (1356–1360), Biosis Abstract AN 1978: 198039.*

* cited by examiner

*Primary Examiner*—Theodore J. Criares
(74) *Attorney, Agent, or Firm*—Browdy and Neimark PLLC

(57) ABSTRACT

A composition for improving the fertility of a male, and/or for improving the quality of the semen produced by a male includes at least one source of folic acid, preferably 0.05–8 mg; at least one source of zinc, preferably 5–50 mg; and optionally one or more of vitamin B12, magnesium, betaine, choline, SAM, vitamin B2, and Vitamin B6; and/or optionally one or more carriers, excipients and/or adjuvants.

14 Claims, No Drawings

PHARMACEUTICAL OR DIETETIC PREPARATION FOR IMPROVEMENT OF FERTILITY AND SPERM QUALITY

The present invention relates to preparations and compositions for improving the fertility of, and/or for improving the quality of the semen produced by, male individuals of mammalian species, including but not limited to human beings.

More in particular, the invention concerns a pharmaceutical or dietetic preparation that after oral intake can increase fertility and improve sperm quality in male animals in general and men in particular.

The preparations and compositions of the invention can inter alia be used to prevent and/or treat, in male individuals of mammalian species including but not limited to human beings, low fertility, disorders in fertility and/or conditions of poor semen quality, including but not limited to phenomena such as low sperm count, aberrations in morphology of the sperm cells, low motility of the sperm cells, or generally low sperm quality.

In one aspect of particular interest, the preparations and compositions of the invention may be used to prevent and/or treat a condition known as male sub-fertility, by which herein is generally meant a failure to conceive after 1 year of unprotected intercourse with the same partner; and in particular with a sperm count of less than 20 million cells/ml and with more than 30% of sperm cells having normal morfology and more than 50% of sperm cells having normal motility.

In another aspect of particular interest, the preparations and compositions of the invention may be used to prevent and/or treat disorders of male fertility and/or conditions of poor semen quality—including but not limited to male subfertility—as may be caused by, and/or as may be associated with, drug therapy.

In yet another aspect of particular interest, the preparations and compositions of the invention are used in animal breeding, e.g. in breeding programs for livestock and other economically important animals, in horse breeding, in breeding of pets and/or in breeding of zoo animals.

Yet other aspects of the invention relate to methods for improving the fertility of, and/or for improving the quality of the semen produced by, a male individual of a mammalion species, including but not limited to human beings.

Further aspects of the invention will become clear from the description given hereinbelow.

Subfertility is a disorder in which a relatively low number of pregnancies (conceptions) result from a certain number of copulations. Subfertility is a major problem in society. More than 14% of the families in many countries of the Western hemisphere experience problems with fertility and it has been reported than this problem may increase in the near future when the decrease in sperm quality as observed in the last decades is extrapolated. Also in animal breeding subfertility has become a matter of concern. In intensive animal breeding programmes, as e.g. applied in horse, cattle and pig breeding an increase of spermcounts has a clear economical advantage.

Subfertility problems have to be distinguished from erectile or libido disorders. To our knowledge no associations have been published between disorders with libido and subfertility.

Subfertility in males may result from genetic disorders, hypothalamic disorders, undescended testis, clinical disorders [cancer of testis, variocele], germ cell aplasia, medical treatment [irradiation, drug treatment e.g. with sulphasalazine, beta-blockers, anabolic steroids], malnutrition (deficiencies in energy/protein or specific nutrition such as food very rich in phytocomponents), diabetes and environmental factors. Male subfertility is generally associated with decreased semen quality, characterised by a diminished number of sperm cells per semen volume (sperm count) and/or an altered morphology and motility of the sperm cells.

Generally, it is an object of the invention to provide a method for improving the fertility of, and/or for improving the quality of the semen produced by a male individual of a mammalian species, and also to provide preparations and/or compositions that can be used in such a method.

In the art, attempts have been made to improve fertility in animals via administration of dietetic preparations.

Landau B. et al., disclosed in Experientia, 1978, 34, (10), 1301–2 that administration of 10 mg folic acid over 30 days did not result in an increase in sperm counts and motility and DNA content of spermatozoa.

Bentivoglio et al. disclosed in Fertil Steril 1993, 60 (4), 698–701 titled *"folinic acid in the treatment of human male infertility"* that administration of 15 mg folinic acid per day during 3 months increases spermatozoa number and fertility in men suffering from round cell idiopathic syndrome. The authors do not refer to the potential effect of lower amounts of folinic acid or other folate sources nor to beneficial effects that could be obtained by administration of zinc.

Recommendations for folate are typically maximall 400 ug per daily dose except for pregnant women who have a history of neural tube defects in their offspring. Higher amounts can only be allowed when prescribed under medical supervision. It is desirable to decrease doses to avoid risks of underdiagnosing vit B12 deficiencies in persons suffering from perniceous anemia.

Considering the dose-response relationships that are typically observed in the pharmaceutical field, the prior art teaches the skilled person that it is highly questionable whether administration of low concentrations of folate alone is still effective in improving semen quality.

The use of a complex of zinc with an amino acid, in particular aspartate, or with orotate for improving libido has been reported in WO 00-011396. No effect on sperm quality is disclosed. Blesbois E. and Mauger I. have reported in Br.Poult.Sci. 1989, 30 (3), 677–685 that a concentration of zinc above 3 $\mu$g per ml storage medium reduced the fertility of fowl seminal plasma.

Sprenger et al, in Contributions to Nephrology (1984), 38, 103–28 disclosed the effect of zinc salts on sexual dysfunction. No reference is made to folic acid or sperm quality.

European patent application 0 194 710 discloses the use of a zinc salt of fructose-1,6 diphosphate for treatment of male infertility. Folic acid is not mentioned.

European patent application 0 534 033 discloses the use of an injected preparation of zinc gluconate to inhibit the generation, maturation, motality and viability of sperm. The teaching of this European application is therefore contrary to the teaching of the present application, in which zinc is used—in combination with folic acid—to increase the generation and/or the maturation and/or the viability of sperm cells. Also, according to the present application, oral administration is preferred.

Tikkiwal et al. disclose in Ind. J. Physiol. Pharmac., Vol. 31, no. 1, January–March 1987, pages 30 ff., that after administration of 220 mg zinc sulphate to males that suffer from idopathic oligospermia, that sperm and the number of spermatozoa having normal morfology and motility improved significantly. No reference is made to an additional effect that could be obtained by (co-)administering low doses of a source of folic acid.

Also, the amount of zinc sulfate administered according to Tikkiwal is very high, as administration of zinc salts is typically limited to amounts of maximally about 30 mg/day.

The research group of R. Steegers have reviewed published prior art literature in Wong, W. Y, et al, Fertil. Steril. 73, (3), 2000, pp 435–442) titled: *"Male factor subfertility; possible causes and the impact of nutritional factors"*.

U.S. Pat. No. 5,523,087 discloses a pharmaceutical preparation for oral intake and treatment of diabetic male sexual dysfunction in terms of libido. It comprises 45–60 parts phytooestrogen (calculated as free aglycon), 10–50 parts beta-sitosterol, 30–100 parts Damiana leaf dry extract, and optionally up to 400 parts phosphatidyl choline, 15 parts vitamin A, 250 parts B1, 300 parts B6, 100 parts E, 300 parts Calcium, 750 parts Magnesium and 100 parts of Zinc.

In the International application WO 98-52555 it is disclosed that a preparation, having N-acetyl cysteine and optionally vit C, E and zinc as active ingredients, improves fertility in males, also in cases of local inflammations and leucospermia. Folic acid is not considered.

It has now been found that the fertility of, and/or the quality of the semen produced by, a male individual of a mammalian species can be improved by administering to said male individual zince and folic acid, in particular in the amounts indicated hereinbelow.

In particular, it has been found that the administration of zinc and folic acid in combination (further) improves fertility in both subfertile individuals as well as fertile individuals. This means that with advantage, the invention may be used not only in fertile and sub-fertile individuals, but also in male individuals suspected to be subfertile and/or at risk of becoming subfertile—i.e. without the need for (prior testing—or more generally by male individuals of couples that want to conceive a baby.

Accordingly, in a first aspect, the invention relates to a preparation or composition for improving the fertility of, and/or for improving the quality of the semen produced by, a male individual of a mammalian species, said composition comprising:
  at least one source of folic acid;
  at least one source of zinc;
and optionally;
  one or more further components (i.e. as outlined below); and/or optionally;
  optionally one or more carriers, excipientia and/or adjuvantia (i.e. as outlined below);
in particular in the amounts indicated hereinbelow.

The invention also relates to a method for improving the fertility of, and/or for improving the quality of the semen produced by, a male individual of a mammalian species, said method comprising administering to said male individual of a mammalian species:
  at least one source of folic acid;
  at least one source of zinc;
  optionally one or more further components;
in particular in the amounts indicated hereinbelow, and more in particular in the form of a preparation or composition as described above.

In yet another aspect, the invention relates to the use of at least one source of folic acid and at least one source of zinc in the preparation of a preparation or composition for improving the fertility of, and/or for improving the quality of the semen produced by, a male individual of a mammalian species, including but not limited to a human being.

Further aspects of the invention will become clear from the further description hereinbelow.

The preparation and/or compositions of the invention may in particular be preparations and/or compositions intended and/or suitable for oral administration to a male individual of a mammalian species, including but not limited to pharmaceutical and/or veterinary preparations or compositions, and/or food supplements, i.e. for humans food or animal feed.

By "a source of folic acid" is generally meant herein a compound that is suitable for administration, and in particular for oral administration, to a male individual of a mammalian species; and that upon such administration provides and/or makes (biologically) available to said individual folic acid, i.e. so as to lead to elevated levels of folic acid in the body of said mammal or at least one part thereof, including but not limited to a suitable biological fluid such as blood, plasma and/or semen (fluid).

Suitable examples of such sources of folic acid include, but are not limited to, folic acid and salts thereof, folate-compounds; or optionally suitable analogs, precursors and/or metabolites of folic acid or folate compound; or any suitable combination thereof. Also, the source(s) in folic acid may be in a suitable reduced or oxidized form, as will be clear to the skilled person.

Some specific examples of suitable source of folic acid include, but are not limited to, mono- or polyglutamate forms of folic acid, salts and/or esters of folic acid, and/or methylated derivatives of folic acid, for instance as folinic acid or 5-methyl tetrahydrofolic acid; or any suitable combination thereof. It is preferred to use the reduced monoglutamate form.

By "a source of zinc" is generally meant herein a compound that is suitable for administration, and in particular for oral administration, to a male individual of a mammalian species; and that upon such administration provides and/or makes (biologically) available to said individual zinc, in particular in the form of $Zn^{2+}$ ions.

Suitable examples of such "bioavailable" sources of zinc will be clear to the skilled person, for instance from the prior art mentioned above, and may for instance include bioavailable zinc salts, including but not limited to salts with anorganic anions such as chloride, carbonate and sulphate, but also zinc salts with organic anions such as lactate, gluconate, fructosephosphates, orotate, citrate, malate, pyruvate, etc. and complexes of zinc with an organic molecule such as an aminoacid, or bi- or tridentate compound; or any suitable combination thereof.

It is preferred to use a non-hygroscopic food-grade ingredient with good organoleptic properties such as zinc sulphate or zinc citrate.

The preparations and/or compositions may optionally contain one or more further components known per se, including but not limited to components which by themselves have some biological, pharmacological and/or veterinary activity, i.e. upon (oral) administration to a male individual of a mammalian species.

In particular, these one or more further components may be one or more compounds that are known per se to have, upon (oral) administration to a male individual of a mammalian species, a beneficial influence on the fertility and/or sperm quality of a male individual of a mammalian species; and/or may be one or more components that, upon (oral) administration to a male individual of a mammalian species, may further increase, enhance and/or facilitate the fertility- and/or semen quality-improving action of the zinc and folic acid that are administered according to the present invention.

The one or more further components used should most preferably be suitable for (oral) administration to a male individual of a mammalian species, and should also be compatible with the other constituents of the preparations and/or compositions of the invention, and in particular with the at least one source of zinc and the at least one source of folic acid used.

For instance, the further component(s) may be one or more compounds which support spermatogenesis or any part and/or pathway of spermatogenesis, such as the so-called "methylation pathway". Some non-limiting example of such compounds include but are not limited to:

magnesium, i.e. in the form of a bioavailable source of magnesium such as a bioavailable magnesium salt, e.g. magnesium citrate;

one or more vitamins, and in particular vitamin B2 and/or vitamin B12;

a suitable source of methyl groups like methionine, betaine and/or choline the latter for instance in the form of phosphatidylcholine or a suitable source thereof such as lecitine;

a suitable methylation agent such as S-adenosyl methionine (SAM); and, if required, a suitable source of glucose;

or any suitable combination thereof.

Such further components may also be one or more compounds which improve levels of (reduced) glutathion in the spermatozoo. Some non-limiting example of such compounds, include, but not are limited to vitamin B6, which may be present/administered in the form of a (stable) pyridoxine or as a derivative thereof, such as pyridoxal or pyridoxamine. Improvement of glutathion status in spermatozoa is important for improving sperm quality, including but not limited to increasing half-life, motility and/or the capacity to facility and egg-cell.

Other suitable components for use in the compositions and preparations of the invention are for instance mentioned in some of the prior art mentioned above, and in particular in WO 99-03365.

The compositions and preparations may also contain a suitable source of copper, and in particular $Cu^{2+}$-ions, such as copper(II) sulphate, copper(II)carbonate or copper(II) citrate.

According to the invention, the source of folic acid, the source of zinc, and optionally the one or more further components, are administered to a male individual of a mammalian species in an amount that, upon such (oral) administration, has a beneficial influence on the fertility of, and/or on the quality of the semen produced by, said individual, most preferably without any adverse side effects and/or health risks to said individual.

It has been found that particularly suitable amounts of administration are between 0.05 and 8 mg, and in particular 0.1 and 6 mg per day for the at least one source of folic acid, in combination with between 5 and 50 mg, and in particular between 10 and 25 mg per day for the at least one source of zinc. The one or more further components mentioned above may be administered in suitable amounts known per se, for instance as indicated in the further description below. The amounts as described above are given for mammals having a body weight of approximately 70 kg; for mammals/vertebrates having a different body weight the above amounts should be corrected for body weight. For instance, for a mammal of 350 kg, the above amounts should be multiplied by a factor 5.

The above amounts may be administered as a single daily dose or as several doses per day. Preferably, for such administration, the source of folic acid, the source of zinc, and the one or more further components are provided/administered essentially simultaneously, and in particular as (part of) a single preparation or composition, but within the same dietetic regimen. However, although not preferred, it is also within the scope of the invention that the source of folic acid, the source of zinc and the one or more further components are administered separately, i.e. as (part of) separate preparations and/or compositions.

Also, it should be noted that any administration as described above must be continued for a period of at least 20 days, and in particular for at least 40 days, and for example (at least) 90 days, before the beneficial effect on the fertility of, and/or on the quality of the semen produced by, the male individual is obtained.

Furthermore, because the bioavailability of folates may differ considerably, the dose of the particular source of folic acid that is administered should be corrected for the bioavailability thereof, as will be clear to the skilled persons. Folates from natural sources demonstrate typically lower bioavailability due to the different form of folate and/or the presence of inhibitors of processes that are essential for good bioavailability.

Also, the administration of the at least one source of folic acid should take into account the sigmoidal dose response curve. In this respect, the use of a combination of zinc and folic acid may allow for the administration of the source of folic acid in low(er) amounts compared to the use of folic acid alone, the administration of which in high(er) doses—i.e. of 10 mg or more—is not desirable.

The compositions and/or preparations of the invention preferably contain the at least one source of folic acid, the at least one source of zinc, and optionally the one or more further components, in amounts that allow the above amounts to be administered, i.e. as one or more doses per day.

Thus, the preparations and/or compositions preferably contain the at least one source of folic acid in an amount of between 0.05 and 8 mg, and preferably of between 0.1 and 6 mg; and contain the at least one source of zinc in an amount of between 5 and 50 mg, and preferably of between 10 and 25 mg. The one or more further components may also be present in suitable amounts, e.g. as indicated below.

Preferably, the at least one source of folic acid, the at least one source of zinc, and optionally the one or more further component are comprised as a unit dose.

Some particularly preferred compositions according to the present invention will be described hereinbelow.

The preparations or compositions of the invention may be in the form suitable for administration, and in particular for oral administration, to a male individual of a mammalian species, including but not limited to a human being. As such, the compositions of the invention may for instance be in the form of:

a pharmaceutical composition suitable for (oral) administration, such as a tablet, powder, capsule, sachet, syrup, elixer; and/or a veterinary composition suitable for (oral) administration to the intended mammal; and/or an additive or supplement for human food or animal feed, such as a concentrate, powder, syrup or premix that is to be mixed with human food or animal feed; and/or a food or food supplement, such as a bar, a fortified food product such as a cereal, sauce, dessert soup, etc; and/or an animal feed.

The formulation/preparation of such preparations or compositions may be carried out in a manner known per se, while will generally comprise combining the at least one source of folic acid, the at least one source of zinc, optionally the one or more further components with each other and optionally with one or more acceptable carriers, excipientia, adjuvants; and/or a suitable food or food base, depending upon the intended final preparation or composition, as will be clear to the skilled person.

The preparation of the invention may also be suitable packaged. The packaging form that is selected depends on the application and form of the preparation and is the choice thereof is known in the art.

Alternatively, as mentioned above, the at least one source of folic acid, the at least one source of zinc, and/or the one or more further components may be administered as (part of) separate compositions or preparations, e.g. intended for combined use in improving the fertility of, and/or for improving the quality of the sperm produced by, a male individual of a mammalian species. Such separate preparations or compositions may be packaged together, i.e. to provide a "kit of parts", and such a kit forms a further aspect of the invention.

The preparations and compositions of the invention may generally be used to improve the fertility of, and/or to improve the quality of the semen produced by, a male individual of a mammalian species, e.g. to improve the changes of reproduction of said male individual and/or to provide the quality of the spemen produced by said male individual.

For instance, the compositions and/or preparations of the invention may be administered to human beings; to economically important animals such as cattle, sheep, pigs and horses; to pets such as cats and dogs; to zoo animals and/or to any other desired mammal. More generally, and in additional the compositions of the invention may also be used in male individual of a non-mammal, vertebrate species, such as species of birds, fowl (i.e chicken), reptiles, and/or fish.

As such, the compositions of the invention may be administered to fertile male individuals, to sub-fertile male individuals, to male individuals which are suspected to be sub-fertile and/or to male individuals which are at (increased) risk of becoming sub-fertile, e.g. due to drug therapy, radiation therapy, disorders of the urogenital tract, and/or due to other factors, such as environmental factors and/or the further factors mentioned above.

For example, in fertile male individuals, increase of sperm counts in fertile male animals may be of interest to increase further the chance of fast reproduction, which can have an economical benefit in animal breeding, but also may have psychological and practical advantages in men.

Also, in fertile male individuals, the invention may be used to provide sperm of improved quality, e.g. for use in animal breeding programs; for use in insemination, IVF and other fertilization techniques; and/or when sperm is to be frozen and stored over longer periods of time.

In sub-fertile male individuals, the compositions of the invention may be used to treat said sub-fertility, i.e. again to enable or at least to improve the chances of successful fertilization.

In another advantageous application, the compositions and preparations of the invention may be administered to a male individual of a mammalian species, and in particular to a human, without it being known a priori whether said male individual is fertile or sub-fertile. For instance, in this application, the compositions of the invention may be administered to the male individual of a couple when fertilization is retarded, e.g. to obviate testing and/or as a first step before any further testing is carried out. This is important since sperm testing is expensive, places a burdon on the individual involved, and because the specificity and sensitivity of testing systems vary, and because there may be fluctuations in sperm count and/or sperm quality.

The compositions of the invention may be also used (i.e. profylactically) by male individuals of couples that are intending to have a baby, i.e. to increase the chances of fertilization and/or to counteract any problems with male fertility that may be present, again without the need of prior testing.

The compositions of the invention may also be used to prevent or counteract the effects on reproduction of fluctuations of sperm count or sperm quality over time.

In yet another important aspect, the compositions and/or preparations may be used profylactically to prevent a decrease in fertility and/or to prevent a decrease in sperm quality in individuals at risk thereof, for instance in male individuals that are (to be) subjected to drug therapy, and in to drug therapy, radiation therapy, individuals suffering from disorders of the urogenital tract, and/or other disorders that may effect fertility and/or sperm quality, such as those mentioned above.

Also, the compositions and/or preparations of the invention may for instance be used to improve fertility and/or to improve sperm quality caused by factors such as malnutrition, environmental factors, and/or exposure to harmful substances.

The invention will now be discussed in more detail below.

The invention concerns a pharmaceutical or dietetic preparation that after oral intake can increase fertility and improve sperm quality in male animals in general and men in particular.

The preferred compositions of the preparations is characterised by the presence of 0.05–8 mg folate and optionally 5–30 mg zinc and/or other components. The preparations can have the form of a powder, a liquid, a bar, a fortified food product such as a cereal, a sauce, a dessert, a soup, etc. The preparation can be a supplement, concentrate, premix or a complete food.

The present invention (also) concerns a preparation to enhance male fertility through increasing the number of sperm cells with no visible and/or detectable aberrations in morphology and motility per semen volume.

In one aspect of the invention the preparations are meant to be used to prevent and treat subfertility in general in male subjects of animals, especially in men.

In another aspect of the invention the preparations can be used in association with drug therapy a radiation therapy, disorders in the urogenital tract and other causes of subfertility as mentioned above.

In a third aspect of the invention it is aimed to increase sperm counts in general. Increase of sperm counts in fertile male animals is of interest to increase further the chance of fast reproduction, which can have an economical benefit in animal breeding, but also may have psychological and practical advantages in men.

In a fourth aspect of the invention it is aimed to develop a preparation that is effective for both fertile and subfertile males at the same time. This is important in order to avoid extensive testing of sperm quality when fertilisation is retarded. This is important since testing is expensive and specificity and sensitivity of testing systems vary, an the fluctuations in time of the sperm count and/or the sperm quality of an individual.

It has been found that a pharmaceutical or dietetic preparation for oral use that comprises per daily dose 0.05–8 mg folate and optionally other components, such as bioavailable zinc salts increases fertility in male animals.

In this document animals are meant to be any (vertebrate) animal including but not limited to humans and/or (other mammals).

Pharmaceutical preparations are meant to be any nutritional product suitable for oral administration. Such preparations can have the form of a powder, a liquid, a bar, a fortified food product such as a cereal, sauce, dessert soup, etc. The preparation can be a supplement, concentrate, premix or a complete food.

The packaging form that is selected depends on the application and form of the preparation and is the choice thereof of known in the art.

It has been found that the preparations according to the invention can be used for improving fertility in male animals. The improvement can be achieved in already fertile animals but also in subfertile animals, especially in subfertile humans, in particular in subfertile men.

It has also thought that the product is useful when used during therapy with certain drugs or radiation or when certain clinical disorders have occurred.

It has been found that the preparations according to the invention can be used for improving fertility in male animals. The improvement can be achieved in already fertile animals but also in subfertile animals, especially in subfertile humans, in particular in subfertile men.

In this document, subfertility in humans is defined as being a condition in which sperm count is less than 80 million sperm cells per milliter semen. The product is also effective in subfertile men demonstrating less than 20 million sperm cells/ml semen (WHO classification), moe in particular in subfertile men demonstrating less than 20 million sperm cells/ml and more than 30% sperm cells with normal morphology and more than 50% of sperm cells with normal motility.

The preparations according to the invention include folate and optionally zinc and other components.

Table 1 demonstrates the relative effectivity of the administration of 5 mg folic acid alone (as oxidixed monoglutamate), 15 mg zinc alone (66 mg as zinc sulphate) and the combination of 5 mg folic acid and 15 mg zinc during three months in either fertile men and subfertile men in terms of spermcount versus the initial situation before the dosage regimen.

TABLE 1

Percentage improvement of spermcount after administration of active agents, compared to initial spermcount.

| | Relative improvement after administration during 5 months of | | |
|---|---|---|---|
| | 5 mg folate | 15 mg zinc | 5 mg folate and 15 mg zinc |
| fertile men | 0 | + | + |
| subfertile men | +++ | ++ | +++(+) |

The number of + signs indicates activity; 0 means about neutral.

It can be concluded that administration of folate alone increases sperm count as in especially subfertile men. On the other hand administration of zinc increases sperm counts in both groups, so also in fertile men.

Without wanting to be bound by theory it is thought that a proper functioning of methylation pathways for a long term, preferably more than 2 months, is essential for proper spermatogenesis. Up to now, no relation is laid in the prior art between fertility and methylation processes or semen quality and metabolic capacity of methylation processes.

As is disclosed in WO 99-03365 methylation pathways could be supported by administration of magnesium, vitamin B12 and a source of methyl groups like methionine or betaine and, if required, a source of glucose. Also the methylation agent S-adenosyl methionine could be used.

Methylation processes may further be supported by administration of vitamin B2.

It is claimed that above-mentioned components, especially magnesium and vitamin B12 improve fertility of male animals.

In the spermatozo relatively high levels of reduced glutathion occur. By the invention it is considered to be essential for survival of the cell during storage and during the time that sperm is underway to the egg cell that glutathion levels are high. WO 99-03365 discloses that administration of vitamin B6 may help. It is claimed that administration of more than 1 mg vitamin B6 per daily doses increases spermatozo glutathion levels.

In this application folate is defined to be those components that after oral ingestion result in elevated folic acid levels—i.e. as increased levels of 5-methyltetrahydrofolate—in the body.

Suitable sources are folic acid and polyglutamate forms esters and methylated derivatives or other metabolites thereof [such as folinic acid or 5-methyl tetrahydrofolic acid] thereof in both reduced and oxidised form. It is preferred to use the reduced monoglutamate form.

Because the bioavailability of folates may differ considerably, the does that is administered is corrected for bioavailability. Folates from natural sources demonstrate typically lower bioavailability due to the different form of folate and/or the presence of inhibitors of processes that are essential for good bioavailability.

The preparations according to the invention should comprise at least 50 ug folate and preferably more than 200 ug and most preferably more than 40 ug per daily dose.

When more than 300 ug folate is administered it is preferred to use a reduced form of folate, because the metabolic capacity in that particular patient/animal may not be sufficient to maintain all folate in plasma in the reduced form.

It is found that not more than 8 mg, and preferably less than 6 mg folate are required for effective support of spermatogenesis without adverse side effects. The optimal amount of folate that should be administered further depends on the inclusion of other components like vitamin B12 and synergistically operating components like zinc and the speed with which one wants to improve fertility.

When more the than 400 ug folate per daily dose is administered also vitamin B12 should be included in the formulation in an amount of more than 1 ug per 400 ug folate and preferably more than 2 ug per 400 ug folate. These amounts also act synergistically in patients/animals suffering from malnutrition or urogenital infections or cancer.

In order to maintain the reduced form of folate during storage and passage through the first part of the intestinal tract, a type of product formulation and packaging is selected which ensures release of high amount of reduced folic acid in the proximal part of the small intestine.

It has been found that the effect of folate on sperm quality is increased when other components, especially zinc, is administered during that same day.

As source of zinc salts can be used any bioavailable source of zinc. These sources include salts with anorganic anions such as chloride, carbonate and sulphate, but also zinc salts with organic anions such as lactate, gluconate, fructosephosphates, orotate, citrate, malate, pyruvate, etc. and complexes of zinc which an organic molecule such as an aminoacid, or bi- or tridentate compound.

It is preferred to use a non-hygroscopic food-grade ingredient with good organoleptic properties such as zinc sulphate or zinc citrate.

Zinc salts or complexes should be included in such an amount that at least 5 mg zinc is available to a patient of about 80 kg and preferably more than 10 mg and most preferably more than 13 mg.

When more than 13 mg zinc is administered per daily dose it is recommended to include a copper source such as copper sulphate or carbonate in order to avoid metabolic imbalances. The ratio of zinc to copper should be in the range of 4–20 and preferably in the range 5–15.

A further beneficial effect can be obtained by including magnesium in the preparation, for example in the form of magnesium citrate.

Magnesium should be administered in an amount of at least 0.7 mg per kilogram bodyweight per day.

In order to avoid imbalances with minerals also calcium should be included when magnesium is administered and in an amount of at least 2 mg calcium.

S-adenosyl methionine (SAM) can be administered in an amount of 0.1–5 g, preferably, 0.2–1 g.

Vitamin B12 is preferably administered as cyanocobalamine but also other cobalamines can be used.

Vitamin B6 can be administered as the stable pyridoxine or as a derivative such as proximal or pyridoxamine.

Betaine is considered to be an important component for the improvement of semen quality of especially the group of males that experience an impaired folate metabolism or require a rapid restoration of sperm quality, so especially subfertile men. It supports the methylation pathways in a way that is independent from folate metabolism.

Betaine can be replace by choline or a source thereof, such as phosphatidycholine or sources thereof such as lecithin.

Betaine should be administered in an amount of 0.5–2.0 g, in particular 1–10 g. The amount of the precursors can be calculated by administering equimolar doses.

Methionine is mandatory for those patients that suffer from subfertility due to malnutrition.

Methionine can be administered as free amino acid or as methionine-rich peptides or proteins, such as casein. The amount of methionine that is consumed per day should be 0.6–6 g and preferably 1.2–3 g.

In Table 2 some preferred compositions of the preparations is summarised.

TABLE 2

Compositions of the preparations according to the invention. Amounts are given per daily dose, either in one preparation or as a combination preparation.
Folate 0.05–8 mg; Zinc 5–50 mg
Preferred: Folate 0.1–6 mg; Zinc 10–25 mg; Vit B12>1 ug
Most preferred: Folate 0.4–5.5 mg; Zinc 13–25 mg; Vit B12>2 ug; Magnesium>50 mg; Copper>1 mg; Vit. B6>1 mg; Methionine equivalents>0.3 mg; Betaine equivalents>0.3 mg

EXAMPLES

Example I

A tablet suitable for use in the present invention was prepared using the following constituents:

| | |
|---|---|
| Folic acid | 600 ug |
| Zinc sulphate | 35 mg |
| Cyanocobalamine | 2 ug |
| Carrier | |

Example II

A 1 g tablet pressed from carriers and aids known in the art and the following active ingredients:

| | |
|---|---|
| Folic acid | 2 mg |
| Zinc sulphate | 66 mg |
| Cyanocobalamine | 8 ug |
| Magnesiumcarbonate | 200 mg |
| Pyridoxine | 2 mg |
| Vitamin B2 | 1.6 mg |

Example III

A powder in sachet form (10 g) was prepared using the following constituents:

| | |
|---|---|
| Soy lecithin | 2 g |
| Casein | 3 g |
| Sucrose | 2 g |
| Folic acid | 1 mg |
| Cyanocobalamin | 10 ug |
| Zinc sulphate | 100 mg |
| Magnesium carbonate | 200 mg |

Instead of 3 g casein, also 1 g casein and 2 g betaine may be used.

Example IV

A powder is sachet form (10 g) was prepared using the following constituents:

| | |
|---|---|
| Soy lecithin | 1 g |
| Casein | 1 g |
| Betaine | 2 g |
| Sucrose | 2 g |
| Methyltetrahydrofolate | 0.7 mg |
| Cyanocobalamin | 10 ug |
| Zinc sulphate | 100 mg |
| Magnesium carbonate | 200 mg |

What is claimed is:
1. Method for improving the fertility of, and/or for improving the sperm count of the semen produced by, a male individual of a mammalian species, said method comprising administering synergistically effective amounts of to said individual at least one source of folic acid in an amount of between 0.05 and 8 mg per day and at least one source of zinc in an amount of between 5 and 50 mg per day.
2. A method according to claim 1 wherein said male is not folate deficient.

3. A method according to claim 2, wherein said male's subfertility is associated with at least one of drug therapy; radiation therapy; diabetes; and variocele disorders of the urogenital tract.

4. The method of claim 1 wherein the method further comprises administering vitamin $B_6$.

5. The method of claim 4 wherein said folic acid is administered in an amount between 0.1 and 6 mg per day, and said zinc is administered in an amount of between 10 and 25 mg per day.

6. The method of claim 1 wherein said folic acid is administered in an amount between 0.1 and 6 mg per day, and said zinc is administered in an amount of between 10 and 25 mg per day.

7. The method of claim 2 wherein said folic acid is administered in an amount between 0.1 and 6 mg per day, and said zinc is administered in an amount of between 10 and 25 mg per day.

8. The method of claim 1 wherein said administration is repeated and continued for at least 20 days.

9. The method of claim 8 wherein said administering is for at least 40 days.

10. The method of claim 8 wherein said administering is for at least 90 days.

11. The method according to claim 2 wherein said male's subfertility is associated with at least one disorder selected from the group consisting of at least one of genetic disorders, hypothalamic disorders, undescended testes, testicular cancer, germ cell aplasia, malnutrition, and environmental factors.

12. The method according to claim 4 wherein the method comprises administering more than 1 microgram vitamin $B_{12}$.

13. The method according to claim 12 wherein the method further comprises administering more than 50 mg magnesium, more than 50 mg betaine, or a mixture of more than 50 mg magnesium and more than 50 mg Betaine.

14. The method according to claim 1 wherein the method further comprises administering at least one of
 a. more than 1 microgram vitamin $B_{12}$;
 b. more than 50 mg magnesium;
 c. more than 50 mg betaine;
 d. more than 50 mg choline or a source of choline in a molar amount that is equivalent to more than 0–0.3 mg betaine; and
 e. 0.1–5 grams S-adenosyl methionine.

* * * * *